(12) United States Patent
Fujino et al.

(10) Patent No.: US 6,355,495 B1
(45) Date of Patent: Mar. 12, 2002

(54) METHOD AND APPARATUS FOR ANALYZING MINUTE FOREIGN SUBSTANCE, AND PROCESS FOR SEMICONDUCTOR ELEMENTS OR LIQUID CRYSTAL ELEMENTS BY USE THEREOF

(75) Inventors: Naohiko Fujino; Isamu Karino; Masahi Ohmori, all of Hyogo; Masatoshi Yasutake; Shigeru Wakiyama, both of Chiba, all of (JP)

(73) Assignees: Mitsubishi Denki Kabushiki Kaisha, Hyogo; Seiko Instruments Inc., Chiba, both of (JP)

( * ) Notice: Subject to any disclaimer, the term of this patent is extended or adjusted under 35 U.S.C. 154(b) by 0 days.

(21) Appl. No.: 09/553,339

(22) Filed: Apr. 20, 2000

Related U.S. Application Data

(63) Continuation of application No. 08/600,142, filed on Feb. 12, 1996, now Pat. No. 6,124,142.

(30) Foreign Application Priority Data

Feb. 14, 1995 (JP) .............................................. 7-025117

(51) Int. Cl.[7] .......................... H01L 21/66; G01R 31/26
(52) U.S. Cl. ............................. 438/18; 438/14; 438/16; 438/17; 356/237
(58) Field of Search .......................... 438/18; 356/237; 458/14, 15, 16, 17

(56) References Cited

U.S. PATENT DOCUMENTS

| | | | |
|---|---|---|---|
| 4,814,842 A | | 3/1989 | Nakagawa et al. ......... 357/23.7 |
| 5,463,459 A | * | 4/1993 | Morioka et al. ............. 356/237 |
| 5,267,017 A | | 11/1993 | Uritsky et al. .............. 356/375 |
| 5,466,325 A | | 11/1995 | Mizuno et al. ............. 156/344 |

FOREIGN PATENT DOCUMENTS

| | | |
|---|---|---|
| EP | 0 633 450 A3 | 1/1995 |
| EP | 0 633 450 A2 | 1/1995 |
| EP | 0 641 021 A2 | 3/1995 |

(List continued on next page.)

OTHER PUBLICATIONS

Takeshi Hattori et al., "An Automated Particle Detection And Indentification System in VLSI Wafer Processing," *Solid State Technology*, 34 (1991) Sep., No. 9, pp. S1–S6.

M.W. Cresswell, et al., "Text Structure for the In–Plane Locations of Projected Features with Nanometer–Level Accuracy Traceable to a Coordinate Measurement System," Proc. IEEE Int. Conference on Microelectronic Test Structures, vol. 6, Mar. 1993.

*Primary Examiner*—David Nelms
*Assistant Examiner*—Reneé R. Berry
(74) *Attorney, Agent, or Firm*—Hogan & Hartson, LLP

(57) ABSTRACT

To provide a minute foreign matter analysis method and device wherein the observation, analysis and estimation of minute foreign matter is permitted by linking the device coordinate of a particle inspection device and those of other analysis devices with by far higher accuracy.

A minute foreign matter analysis method comprising the steps of: determining the position of a minute foreign substance on the surface of a sample in a particle test unit; transferring said sample onto a coordinate stage of an analysis unit; inputting the position determined by said particle test unit for the minute foreign substance to the coordinate stage of the analysis unit; and analyzing the contents of the relevant minute foreign substance wherein at least one of the unit coordinate to be employed in said particle test unit and the unit coordinate to be employed in said analysis unit is previously corrected using a standard wafer which has a scale on the surface so that coordination systems of said particle test unit and said analysis unit can be linked each other.

10 Claims, 9 Drawing Sheets

FOREIGN PATENT DOCUMENTS

| | | |
|---|---|---|
| EP | 0 641 021 A3 | 3/1995 |
| JP | 60-218845 | 11/1985 |
| JP | 61162737 | 7/1986 |
| JP | 62-263646 | 11/1987 |
| JP | 63240040 | 10/1988 |
| JP | 3-156947 | 7/1991 |
| JP | 3-181848 | 8/1991 |
| JP | 04123454 | 4/1992 |
| JP | 6-120311 | 4/1994 |
| JP | 6-258047 | 9/1994 |
| JP | 6-317536 | 11/1994 |
| JP | 6-324003 | 11/1994 |
| JP | 7-5407 | 1/1995 |

\* cited by examiner

○ : 3 μm o : 5 μm

------- : 1 μm

METHOD AND APPARATUS FOR ANALYZING MINUTE FOREIGN SUBSTANCE, AND PROCESS FOR SEMICONDUCTOR ELEMENTS OR LIQUID CRYSTAL ELEMENTS BY USE THEREOF

This is a continuation of application Ser. No. 08/600,142 filed Feb. 12, 1996, which application is hereby incorporated by reference in its entirety now U.S. Pat. No. 6,124,142.

BACKGROUND OF THE INVENTION

The present invention relates to a method and an analyzer for analyzing a minute foreign substance present on the surface of a planar sample such as e.g., a silicon wafer for semiconductor element or an insulating transparent substrate for liquid crystal display element, as well as a process for semiconductor elements and liquid crystal display elements by use thereof. More specifically, the invention relates to a method and an apparatus, and semiconductor and liquid crystal display elements by use thereof, in which a minute foreign substance is detected by a particle test unit whose coordinate system is predefined, and by linking the identified position of the minute foreign substance with the coordination system of an analytical unit, it is possible to easily analyze, test and evaluate the identified minute foreign substance.

Analyzers referred to as here mean analyzers for investigating the color tone, stereoscopic image, elemental analysis, chemical structure, crystalline structure and the like by irradiating energy such as light, X-ray, electromagnetic wave, and various corpuscular beams including electron, neutral chemical species (atom, molecule and such others), ion and phonon to the surface of a sample and detecting a secondary corpuscular beam absorbed or radiated due to the interaction with the sample, or treating the surface of a sample, and include units such functions as analysis, test, estimation and treatment, represented by, for example, Metallographical Microscope, Laser Microscope, Probe Microscope, Inter-Atomic Force Microscope (hereinafter, referred to as AFM), Scanning Tunnel Microscope (hereinafter, referred to as STM), Magnetic Force Microscope (hereinafter, referred to as MFM), Scanning Electron Microscope (hereinafter, referred to as SEM), Electron Probe Micro-Analyzer (hereinafter, referred to as EPMA), X-ray Photoelectron Spectrometer (hereinafter, referred to as XPS), Ultraviolet Photoelectron Spectrometer (hereinafter, referred to as UPS), Secondary Ion Mass Spectrometer (hereinafter, referred to as SIMS), Time of Flight-SIMS (hereinafter, referred to as TOF-SIMS), Scanning Auger Electron Spectrometer (hereinafter, referred to as SAM), Auger Electron Spectrometer (hereinafter, referred to as AES), Reflection High Energy Electron Diffraction Spectrometer (hereinafter, referred to as RHEED), High Energy Electron Diffraction Spectrometer (hereinafter, referred to as HEED), Low Energy Electron Diffraction Spectrometer (hereinafter, referred to as LEED), Electron Energy-Loss Spectrometer (hereinafter, referred to as EELS), Focused Ion Beam Instrument (hereinafter, referred to as FIB), Particle Induced X-ray Emission (hereinafter, referred to as PIXE), Microscopic Fourier Transfer Infrared Spectrometer (hereinafter, referred to as Microscopic FT-IR) and Microscopic Raman, as well as observation units, analytical units, test units and estimation units.

The yield in the production of very highly integrated LSI, represented by 4M bit- and 16M bit-DRAM is said to depend almost primarily on defects originating in wafer-adhered foreign substances.

That is because, with finer pattern width, foreign substances of minute size adhered to a wafer in the production process of the previous step, though having so far not been out of the question, becomes the source of pollution. Generally, the size of such minute foreign substances to come into question is said to be on the order of several tenth of the minimum wiring width of very highly integrated LSI to be manufactured, and accordingly minute foreign substances of 0.1 µm level are the object of examination in 16M bit-DRAM (minimum wiring width 0.5 µm). Such minute foreign substances form contaminants and cause disconnection or short of a circuit pattern, greatly leading to the occurrence of faults and a decrease in quality and reliability. Thus, it is a key point to the promotion of yield to grasp and control the actual condition of adhesion and the like of minute foreign substances by accurate measurement and analysis.

As means for this operation, there have conventionally been employed particle test devices capable of detecting the location of a minute foreign substance on the surface of a planar sample, such as silicon wafer. The conventional particle test devices include IS-2000 and LS-6000 available from Hitachi Denshi Engineering Ltd.; Surfscan 6200 available from Tencor, USA; WIS-9000 available from Estek, USA or the like. Meanwhile, on the measuring principle employed for these particle test devices and device configuration for implementation thereof, detailed description is seen, for example, in a literature entitled "Analysis/Estimation Technique for High-Performance Semiconductor Process", pp.111–129, edited by Handotai Kiban Kenkyukai (Semiconductor Substrate Research Group), Realize Ltd.

FIG. 8 shows a display screen of CRT displaying the results measured by using a particle test device LS-6000 for minute foreign substances (0.1 µm or larger) present on an actual 6-inch silicon wafer. That is, this display screen indicates only the approximate position, the number of foreign substances for each size and the distribution of grain sizes. The circle shown in FIG. 8 represents the outer periphery of a 6-inch silicon wafer and points present in the circle correspond to the respective locations of minute foreign substances. Incidentally, a particle or a foreign substance described here means any different portion such as a concave, convex, adhered particle or defect, which generates a scattering (irregular reflection) of light.

As seen also from FIG. 8, however, the information obtained from a conventional particle test device relates only to the size and location of a minute foreign substance present on the surface of such a sample as silicon wafer, and consequently does not permit one to identify an actual state of the relevant minute foreign substance, such as what it is.

As one example, FIG. 4 shows the basic configuration of a conventional metallographical microscope with an actuator, one example of conventional metallographical microscope with a positioning function employed for the detection of a minute foreign substance as observed in the IC testing microscopic instrument MODER: IM-120 available from Nidec Co. Ltd. In FIG. 4, a sample of silicon wafer 2 is placed on an x-y actuator 1 having a coordinate system roughly linked with that of a particle testing device. The foreign substance 7 detected by the particle testing device is so arranged as to be conveyed to the visual field of a metallographical microscope 3 or the vicinity thereof on the basis of the positional information about the foreign substance obtained from the particle testing device. Hereinafter, the testing procedure and tested results for testing a foreign substance 7 present on the surface of a planar silicon wafer by using a conventional metallographical microscope equipped with actuator.

First, with a plurality of slightly stained mirror-surface ground silicon wafers 2 (CZ (plane orientation: 100) 6-inch diameter silicon wafer, available from Mitsubishi Material Silicon) is put on a particle test device (Surfscan 6200, available from Tencor Ltd., USA), the approximate size and the approximate location of a foreign substance present on the silicon wafer 2 are observed. At random positions on the silicon wafer 2, there were about 800 foreign substances in 0.1–0.2 μm level of diameter, about 130 foreign substances in 0.2–0.3 μm level of diameter, about 30 foreign substances in 0.3–0.4 μm level of diameter, about 13 foreign substances in 0.4–0.5 μm level of diameter, and about 15 foreign substances in 0.5 μm or more level of diameter. The coordinate system in Surfscan 6200 is so defined that, letting the x- and y-axes (or y- and x-axes) be the direction in contact with the orientation flat (hereinafter, referred to as "orifla") and its vertical direction in the surface of a wafer, respectively, three points or more of the outermost, except for the part of orifla, are measured and the center position (0, 0) of the wafer is determined by calculating the measured coordinates with the formula of a circle or ellipse.

Next, a conventional metallographical microscopic is employed, in which by letting the x- and y-axes (or y- and x-axes) be the direction in contact with the orifla and its vertical direction in the surface of a wafer, respectively, measuring three points or more of the outermost, except for the part of orifla, and applying the formula of a circle or ellipse to the measured coordinates, the center position of the wafer is determined in the form of (0, 0). After setting a silicon wafer 2 on an x-y actuator 1, an attempt was made to observe foreign substances of individual sizes with a metallogical microscope 3 by operating an x-y actuator on the basis of the positional information about the foreign substance obtained from the particle test device (estimated and observed with the magnification of an eyepiece fixes to 10 and that of an objective varied to 5, 20 and 50).

As a result, foreign substances of 0.4–0.5 μm level diameter could barely be detected as dark points in the case of using an objective of 5 magnitude in the metallographical microscope and those of smaller level diameter could hardly be detected. More specifically, all those of 0.4 μm or larger level diameter could be detected. On the other hand, in the case of using an objective of 50 magnitude, a foreign substance of 0.2–0.3 μm level diameter could rarely be detected as a dark point, but hardly any foreign substance of smaller level diameter could be detected. Thus, to examine the cause, the deviated amounts of coordination in this case were surveyed using a plurality of check-patterned wafers, which revealed that there were deviated amounts of about (±250 μm, ±250 μm) relative to the original position or the center position of the wafer and any point definable in the wafer in the representation of x-y coordinates.

Meanwhile, the visual field for an objective 5 of magnitude the device used at this time was about 1500 μm Φ, whereas that for an objective 50 of magnitude was only about 150 μm Φ.

That is, the reason why many foreign substances of 0.2–0.3 μm level diameter could be selected for an objective of 50 magnitude was found to be that the deviation relatively exceeded the extent of visual field of a microscope due to a change in magnitude from 5 to 50, a high magnitude, and a foreign substance of 0.2–0.3 μm level diameter in question was not included within the visual field of an existing device.

For this reason, it becomes necessary to identify the actual conditions of individual foreign substances through a direct observation or composition analysis by using an appropriate analysis device such as SEM. However, because of being defined in the device coordinate system of a particle test device, locations of individual foreign substances on a wafer do not always coincide with device coordinates of other analysis devices than the particle test device such as SEM. In addition, in setting such a sample as wafer on other analysis devices than the particle test device such as SEM, a coordinate deviation error accompanying a new setting cannot be avoided from occurring. Thus, it is necessary in identifying the actual condition of minute foreign substances to link the device coordinate system of a particle test device with that of a different analysis device such as SEM from the particle test device with high accuracy.

Accordingly, device coordinate systems were investigated for individual particle test devices and different analysis devices such as SEM from the particle test devices. As a result, it was found that the x-y coordinate system is adopted in almost all devices. In determining the coordinate axes and the origin position of each device for a wafer as sample to be measured, there is employed (1) a method for defining the direction of a wafer being in contact with the orifla as the x-axis (or y-axis), its vertical direction in the plane of a wafer as the y-axis (or x-axis) and the interceptions of the y-axis with the outermost periphery of the wafer and with the x-axis respectively as (0, y) and as (0, 0) (cf. FIG. 9(a)), or (2) a method for defining the direction of a wafer being in contact with the orifla as the x-axis (or y-axis), its vertical direction in the plane of a wafer as the y-axis (or x-axis) and the center coordinate of the wafer as (0, 0) by measuring three sample points or more of the outermost circumference and applying the formula of a circle or ellipse to the measured coordinates (cf. Figure (9)b).

In these methods, however, the defined coordinate systems themselves are diverse because the function employed in the definition of coordinate system differs with individual devices or because the number of sample points differs with individual devices. Furthermore, on account of stage error intrinsic in an x-y stage, dependent on the stage accuracy of each device (an actual x-y stage comes to have a somewhat distorted coordinate system relative to the ideal x-y stage as shown in FIG. 3 and this means a differential $e_i$) or an indefinite individual error based on the peculiarity of each device, a deviation occurs without fail in the coordinate axes and origin position of a device coordinate system for a conventional simple "coordinate linking method by inputting the positional information about minute defects or foreign substances detected by a particle test device to the coordinate system of a different analysis device such as SEM from the particle test device". In other words, it is required in examining a minute substance to elevate the magnitude, but the visual field of a test region or analysis region becomes narrower with increasing magnitude.

Thus, at the analyzable magnitude for minute foreign substances of an analysis device, it becomes impossible to set a minute defect or substance within the visual field of the device at that time. That is, it is required in examining a minute substance to elevate the magnitude, but the visual field of a test region or analysis region becomes narrower with increasing magnitude.

Then, deviations of coordinates occurring for the above reason were examined for various device by using a plurality of check-patterned wafers. It was found that, even between well accurate devices (particle test device IS-2000 available from Hitachi Denshi Engineering K.K. and length measuring SEM S-7000 available from Hitachi Ltd.), there were deviated amounts of about (±100 μm, ±100 μm) relative to the origin position or the center position of the wafer and any point definable in the wafer in the representation of x-y coordinates. Accordingly, in analyzing and estimating a minute foreign substance situated at any position on a wafer detected by a particle test device by using a different analytical device from the particle test device, observation or analysis and estimation of the minute foreign substance must be carried out by certain methods of such as magnifying the relevant portion after executing observations in an area (200 $\mu m \times 200$ $\mu m = 40,000$ $\mu m^2$, visual field of the SEM at a 500 magnitude) covering the extent of above ($\pm 100$ $\mu m$, $\pm 100$ $\mu m$) centered at a position on which a foreign substance detected by the particle test device is presumed to be present and ensuring the position of the minute foreign substance. Thus, a fairly long period of time is required.

For intuitively grasping what size relation this area has to a minute foreign substance, an attempt was made to examine the presumably detectable size of a minute foreign substance by calculating the detectable extent (area) one pixel of the CCD camera occupies on the assumption that a CCD camera of 1,000,000 pixels regarded at present as a relatively high-resolution CCD camera was employed for observation. The detectable area that one pixel occupies under the above conditions was calculated to be 0.04 $\mu m^2$ (40,000 $\mu m^2 \div 1,000,000 = 0.2$ $\mu m \times 0.2$ $\mu m$). On the other hand, since it is difficult to discern an object of smaller size than one pixel, the detectable limit of minute foreign substances proves to be 0.04 $\mu m^2$ (0.2 $\mu m \times 0.2$ $\mu m$). That is, it is found difficult to directly detect a foreign substance having a projected area of smaller than 0.04 $\mu m^2$ (about 0.2 $\mu m$ in diameter) by using a CCD camera of 1,000,000 pixels, and extremely difficult to identify the position of the minute foreign substance. Still less, it is nearly impossible to identify the position of a minute foreign substance, 0.2 $\mu m$ or smaller in diameter.

From this, it is deduced generally difficult to identify the position of a minute foreign substance, 0.2 $\mu m$ or smaller in diameter conventionally detected by a particle test device and directly observe or estimate the minute foreign substance by linking the minute foreign substance with the device coordinate system of a different analytical device such as SEM from the particle test device based on the device coordinate system of the particle test device.

SUMMARY OF THE INVENTION

For solving such problems, it is an object of the present invention to provide a minute foreign matter analysis method and device wherein the observation, analysis and estimation of minute foreign matter is permitted by employing a means for linking the device coordinate system of a particle test device with that of a different analytical device such as SEM from the particle device with by far higher accuracy.

It is another object of the present invention to provide a process for a semiconductor element or liquid crystal display element wherein the yield and reliability of a semiconductor element or liquid crystal display element are promoted by testing and analyzing a minute foreign substance in the step of manufacturing a semiconductor element or liquid crystal display element through the above analytical method.

The minute foreign substance analysis method as set forth in claim 1 is a method comprising the steps of: determining the position of a minute foreign substance on the surface of a sample in a particle test unit; transferring said sample onto a coordinate stage of an analysis unit; inputting the position determined by said particle test unit for the minute foreign substance to the coordinate stage of the analysis unit; and analyzing the contents of the relevant minute foreign substance wherein at least one of the unit coordinate to be employed in said particle test unit and the unit coordinate to be employed in said analysis unit is previously measured using a standard wafer with a relatively positioned dot arrow provided on the surface to determine an error of the above unit coordinate system and the unit coordinate system of the above particle test unit and that of the above analytical unit are linked with each other by correcting the error relative to the above unit coordinate systems.

In correcting the unit coordinate by using the above standard wafer, it is preferable for minimizing the error to employ the same standard wafer both for the particle test unit and for the analytical unit.

The minute foreign matter analysis method as set forth in claim 3 is a method comprising the steps of: determining the position of a minute matter on the surface of a sample in a particle test unit; transferring said sample onto a coordinate stage of an analytical unit; inputting the position determined by said particle test unit to the coordinate stage of the analysis unit; and analyzing the contents of the relevant minute foreign substance; wherein the relative positional relation between the dots on the unit coordinate system is determined by detecting the positions of dots on a standard wafer in said particle test unit, the relative positional relation between the dots on the unit coordinate system is determined by detecting the positions of dots on said standard wafer in said analytical unit, and the unit coordinate systems of said both units are linked with each other by comparing the respective relative positional relations of said both units.

In the above standard wafer, since the respective dots of said dot array having a relative positional relation are provided randomly and the positional relation between the respective dots is accurately grasped, the formation of dots is easy.

In the above standard wafer, since the respective dots of said dot array having a relative positional relation are determined by a function defined digitally, the correction of the unit coordinate can be treated using the digitally defined function and thus is easy.

Since the respective dots of the above dot array are provided at least for every certain angle on a circle or for every certain interval on a rectangular-coordinate axis, the correction of the unit coordinate can be treated more easily.

In the above dot array, a set of dots comprises dots having different diameters and accordingly it becomes possible to distinguish whether a set of dots is a variation due to pollution or an original set as intended even if a standard wafer is polluted by foreign substances of any sizes, because the diameters and arrangement of individual dots in an array of dots used for the standard wafer are known. In addition, since a set of dots is formed, information as a measure on a scale can be given to an array of dots.

The above sample may be a semiconductor element in an intermediate step of production or a semiconductor wafer during the forming of said element.

The above sample may be a liquid crystal display element in an intermediate step of production or an insulating transparent substrate during the forming of said element.

The minute foreign substance analytical unit according to the present invention is an analytical unit for placing a sample on a stage after the position of a minute foreign substance in the sample is detected by a particle test unit and analyzing the minute foreign substance, additionally comprising: means for finding a variation tendency of the total error, forming the whole error of said analytical unit by using the relative positional relation of dots on a standard wafer; and means for executing a coordinate correction by subtracting the total error from the unit coordinate based on the variation tendency of said total error.

The above means for finding a variation tendency may comprise means for measuring the position of each dot and determining an error from its true value and means for computing the total error of said unit from said errors of measured positions on the basis of a function defined digitally in possession of each dot of said standard wafer.

The particle test unit according to the present invention is a particle test unit for detecting a minute foreign substance on a sample, additionally comprising: means for finding a variation tendency of the total error forming the whole error of said particle test unit by using the relative positional relation of dots on a standard wafer; and means for executing a coordinate correction by subtracting the total error from the unit coordinate based on the variation tendency of said total error.

The above analytical units in the above each analytical method or the above analytical units may be at least one type selected from a group comprising; scanning electron microscope, metallographical microscope, scanning laser microscope, IR microspectroscope for analyzing the chemical structure, Raman microspectroscope, photoluminescence unit for fluorescent spectroscopy, electron beam probe microanalyzer for surface trace element analysis, Auger electron spectrometer, electron energy-loss spectrometer, secondary ion mass spectroscope, time of flight mass spectrometer, particle induced X-ray spectrometer, reflection high energy electron diffraction spectrometer for crystal analysis, focused ion analyzer for surface treatment, X-ray photoelectron spectrometer for chemical structure analysis, UV photoelectron spectrometer, scanning probe microscope, interatomic force microscope, scanning tunnel microscope and magnetic force microscope.

The process for a semiconductor element according to the present invention is a process for a semiconductor element comprising steps including at least the cleansing step, the film forming step, the exposure step, the etching step, the ion injection step, the diffusion step and the heat treatment step, wherein at least one step of said all steps is accompanied by test steps and at least one of said test steps is for the purpose of analyzing a minute foreign substance in accordance with the method as set forth in claim 1 or by using the unit as set forth in another claim.

The process for a liquid crystal display element according to the present invention is a process for a liquid crystal display element comprising the steps of: pasting a TFT substrate with at least a thin-film transistor and a pixel electrode provided on an insulating transparent substrate and an opposed substrate with at least an opposed electrode provided on an insulating transparent substrate at their peripheries together while keeping a fixed gap; and injecting liquid crystal material into said gap; wherein at least one step of the cleansing step, the film forming step, the exposure step, the etching step, and the ion injection step, constituting the production step of said TFT substrate or said opposed substrate is accompanied by test steps and at least one of said test steps is for the purpose of analyzing a minute foreign substance in accordance with the method described in claim 1 or by using the unit as set forth in another claim.

According to the minute foreign substance analytical method as set forth in claim 1, since the unit coordinate(s) of a particle test unit and/or analytical units is (are) corrected by using a standard wafer with a relatively positioned dot array provided on the surface, the total error equal to the sum of the stage error potentially possessed by the unit coordinate(s) and indefinite individual errors originating in peculiarities of the respective units can be effectively corrected. Thus, the position of a minute foreign substance present on a sample can be accurately identified on the basis of a relative positional relation of individual dots (hereinafter, referred to as scale) in a standard wafer and the place of the minute foreign substance detected by a particle test unit can be immediately set up in the visual field of an analytical unit even if the respective coordinate systems have potential errors between different units, so that analysis can be easily carried out.

According to the analytical method as set forth in claim 2, since correction of both units is made by using one and the same standard wafer, the unit coordinate systems can be conformed to the same standard between both units and can be completely linked with each other.

According to the analytical method as set forth in claim 3, since the relative positional relation between the dots of a standard wafer and the unit coordinates is determined in each of a particle test unit and an analytical unit, and the unit coordinate systems of both units are linked with each other by comparing the respective relative positional relations for both units, it is unnecessary to correct the unit coordinate separately in each unit, the unit coordinate systems are linked with each other between both units and the place of the minute foreign substance detected by a particle test unit can be immediately set up in the visual field of an analytical unit, so that analysis can be easily carried out.

According to the analytical method as set forth in another claim, since the dot array of a standard wafer is provided at random, production of a standard wafer is easy, whereas the relative positional relation between the respective dots is accurately grasped, so that correction of each unit coordinate and linage between both unit coordinates can be easily carried out.

According to the analytical method as set forth in another claim, since the dot array of a standard wafer is determined by a digitally defied function, the total error of each unit can be determined by computation, so that correction of each unit coordinate and linage between both unit coordinates can be easily carried out.

According to the analytical method as set forth in another claim 6, since the respective dots of a dot array are provided for every certain angle on a circle or for every certain interval on a rectangular-coordinate axis, each coordinate in the direction of rotation and the directions of the x- and y-axes can be more easily corrected. Incidentally, if the relative positional relation between individual dots is known, any discrete mathematical definition will do.

According to the analytical method as set forth in another claim, since the respective dots of a dot array employed for the scale of a standard wafer comprise a set of dots having different diameters, it is possible to distinguish whether a set of dots is a result of noise due to pollution or an original set of dots as intended on the standard wafer, even if a standard wafer should be polluted by foreign substances of any sizes, by making sure of the diameters and arrangement of individual dots in an array of dots used for the standard wafer and accordingly it is facilitated to read a coordinate, so that a strict correction can be carried out using a standard wafer. In addition, since a set of dots is formed, information as a measure on a scale can be given to an array of dots.

According to the analytical method as set forth in another claim, since minute foreign substances of a semiconductor wafer in an intermediate step of production can be analyzed, the cause of faults in the production step of a semiconductor element can be analyzed.

According to the analytical method as set forth in another claim, since minute foreign substances of the insulating transparent substrate during the formation of a liquid crystal display element can be analyzed, the cause of faults in the production step of a liquid crystal display element can be analyzed.

According to the method or device as set forth in another claim, surface shape, element, chemical structure, crystalline structure, etc., of minute foreign substances can be analyzed, and also, surface treatment can be performed by selecting analytical unit.

According to the particle test unit and the analytical unit as set forth in another claims, since means is provided for correcting the total error potentially contained in the unit coordinate system based on the scale of the standard wafer, it is possible to decrease the affect of the total error potentially contained in the particle test unit and/or the analytical unit, the position of minute foreign substances containing error detected by the particle test unit is linked accurately to the unit coordinate system of the analytical unit, and the minute foreign substance can be easily set within the field of view of the analytical unit.

According to the analytical unit as set forth in another claim, the means for finding a variation tendency comprises means for determining an error of each dot and means for computing the total error, the total error of each unit can be simply determined.

According to the process for semiconductor elements as set forth in another claims, since the status of a minute foreign substance on the surface of a wafer can be examined at any time during the production step by a sampling test or a total test, the circumstances of occurrence or the cause of occurrence of a minute foreign substance in the production step can be known and be fed back to the production step. As a result, demerits due to minute foreign substances can be minimized even in VLSI where wiring is on the order of submicron, thereby promoting the yield and the reliability as well.

According to the process for liquid crystal elements as set forth in another claims, since the status of a minute foreign substance can be grasped during the forming step of. thin-film transistors, signal wiring or the like, accidents such as break down of a wire even in a liquid crystal element of fine wiring accompanied by a more highly miniaturization can be prevented so that the yield and the reliability of liquid crystal elements can be promoted.

DETAILED DESCRIPTION OF THE INVENTION

Hereinafter, a method and a device for analyzing a minute foreign substance as well as a process by use thereof for semiconductor elements or liquid crystal display elements will be described.

Embodiment 1

As described above, even if the unit coordinate of the particle unit is united with that of the analytic unit by linkage of coordinate systems of both units in order to link the minute foreign substance detected by a particle test unit based on the unit coordinate and identify the minute foreign substance by using an analytical unit, the relevant minute foreign substance cannot be easily aligned within the visual field of the analytic unit. To eliminate the cause for it and accomplish the alignment of a minute foreign substance easily and accurately between both units, the present inventors repeated an intensive study and finally found that the total error containing a stage error intrinsic in the stage of each unit and an indefinite individual error due to the peculiarity of each unit is potentially present in each unit. This total error differs not only between a particle test unit and an analytical unit but is present between different analytical units as errors peculiar to individual units. Thus, they found that the positional coordinates cannot be perfectly linked without linking the coordinate systems themselves in the units with the reference coordinate system not only by linking the coordinate system of the sample with that of each unit and made it possible to reduce the errors of coordinates between the units either by removing the total error of each unit through aids of a standard wafer as the measure having an absolute scale or by comparing the relative positional relations of the respective units relative to a standard wafer, and to readily align a minute foreign substance for all units.

Figure 2:
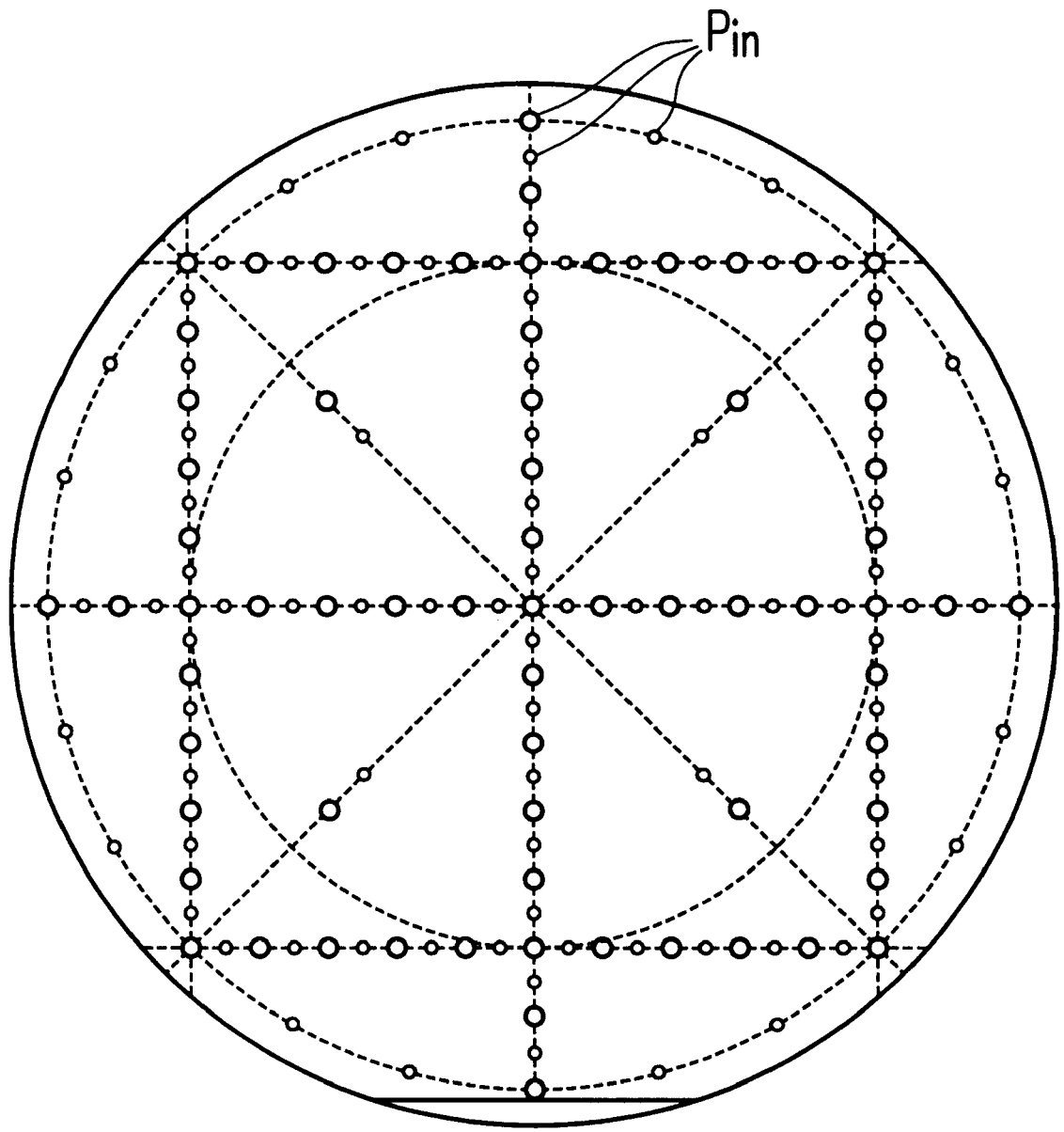
FIG. 2 shows one embodiment of scale pattern provided on the surface of a standard wafer.

As seen from one embodiment shown in FIG. 2, a standard wafer has dots drawn either at intervals of one per deg. on a circle with the origin located approximately at the center of the wafer or at intervals of one per mm on an axis approximately in parallel with or at a right angle to the orifla passing through the origin. The dots are relatively positioned in an array that may be formed by a plurality of array segments, as shown in FIG. 2.

Incidentally, the standard wafer is not restricted to the patterns described here but may be any pattern for indicating the positional relation. However, an array of dots provided on the basis of a functional scale using the discrete mathematics, for example, at intervals of fixed angles on one and the same circle or at intervals of fixed distance respectively along perpendicular directions for the center is desired because the relative positional relation of the respective arrays of positions detected by a particle test unit and analytical units also has a form near to the above function on account of its capability of grasping the relative positional relation of individual dots by using a coordinate system and accordingly errors can be easily found and thus the angle of rotation or the distance in the x- and y-axes can be accurately corrected.

In the example shown in FIG. 2, since dots are provided according to classified diameters of 1 μm, 3 μm and 5 μm, alignment can be made with dots of a larger diameter for a rough correction, whereas a minute correction can be made with dots of a smaller diameter for the fine correction of coordinates.

In addition, by forming an array of dots with a set of dots having different diameters, it is possible to distinguish whether a set of dots is a result of noise due to pollution or an original set of dots as intended on the standard wafer, even if a standard wafer should be polluted by foreign substances of any sizes, by making sure of the diameters and arrangement of individual dots in an array of dots used for the standard wafer and accordingly it is facilitated to read a coordinate, so that a strict correction can be carried out using a standard wafer. In addition, since a set of dots is set up, information as a measure on a scale can be given to an array of dots.

Figure 1:
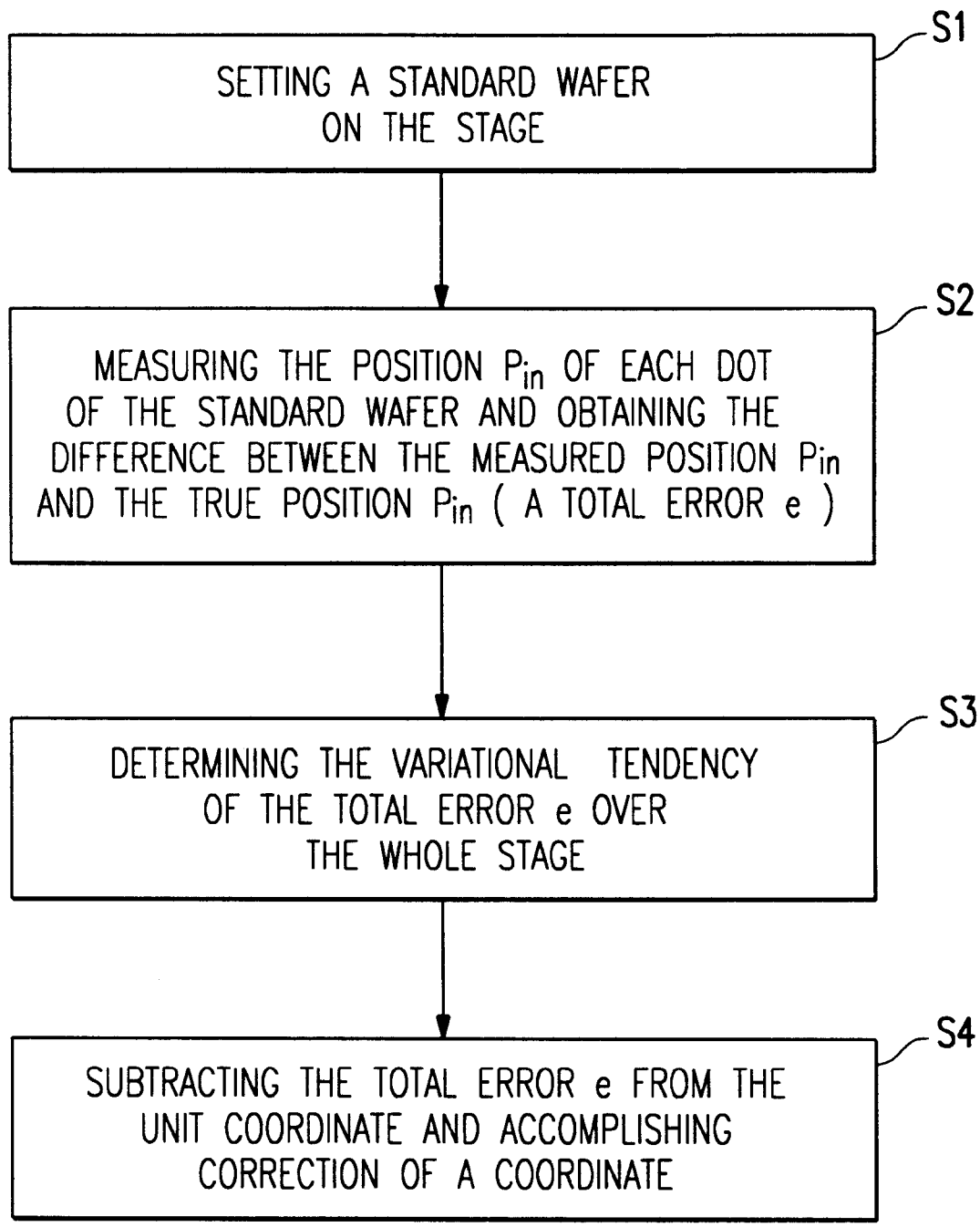
FIG. 1 is a flowchart for correcting the unit coordinate of each unit by using a standard wafer in a analytical method and analytical units according to the present invention.

Hereinafter, a method for estimating the total error composed of the stage error and individual errors and a correction method will be described referring to FIG. 1.

(1) Setting a standard wafer on the stage of each unit, the position $P_{in}$ of each dot (cf FIG. 2) drawn on the wafer is measured respectively (cf. S1 of FIG. 1), where a method for setting a wafer is the same as a conventional one and for example, it is allowable either to match the orifla portion to the direction of the x-axis and take the center as the origin or to orient the wafer in any direction.

(2) The relative positional relation on the unit coordination system of individual dots measured on the coordinate system of each unit coincides with that of an array of dots in the standard wafer. The position $P_{in}$ of each dot measured in individual unit has a value containing the total error $e$ composed of the stage errors and individual errors of individual units. Thus, the total error $e$ composed of the stage errors and individual errors is found as a difference between the measured position $P_{in}$ and the true position $P_{in}$ of a dot (position obtained by overlapping on $P_{in}$ through aids of equations of translation and rotation in contrast to the position defined by an equation of a circle or an equation of a straight line based on the discrete mathematics on the standard wafer) (cf S2).

Figure 3A:
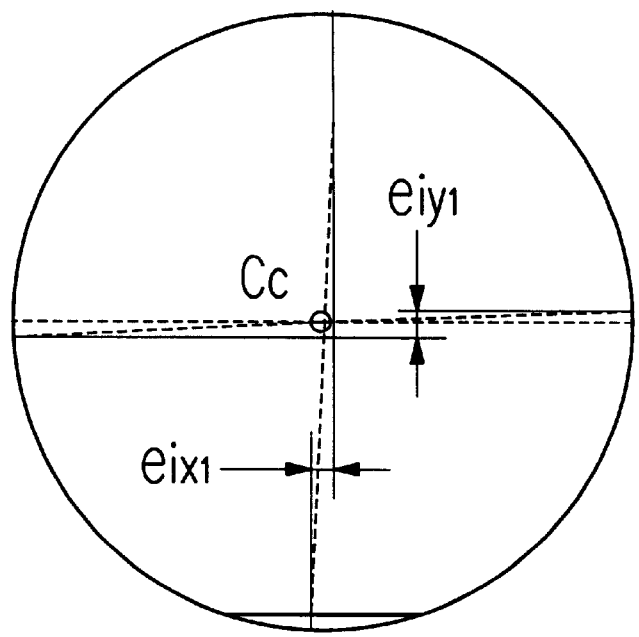
FIG. 3 explains one example of stage error present in a unit coordinate.
Figure 3B:
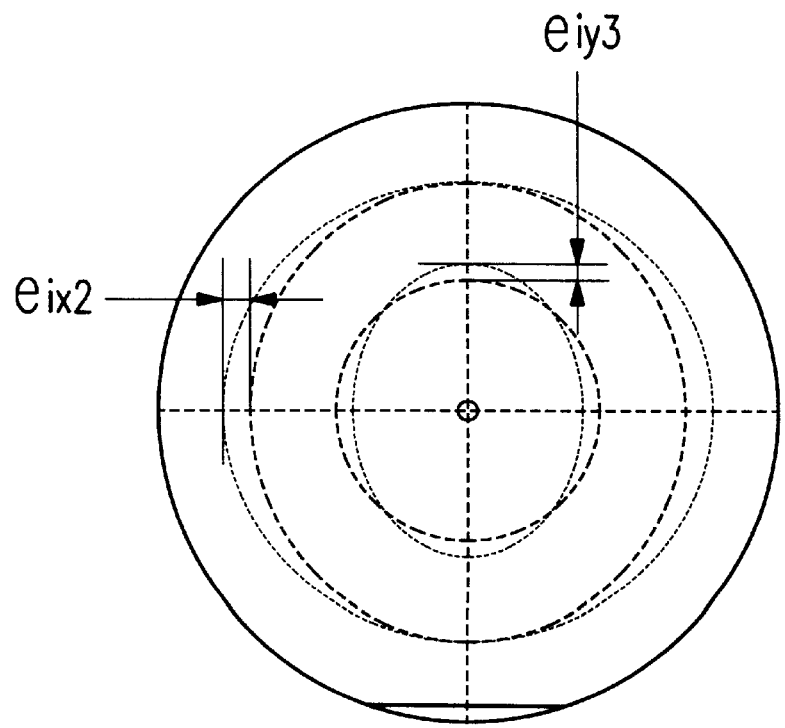

(3) Next, the variational tendency of the total error $e$ over the whole stage is determined by using the total error $e$ on the coordinate of the respective unit in which each dot is measured. Since the total error $e$ over the whole stage is considered to vary continuously, the absolute value of the total error $e_{xy}$ at specified positions x, y on the coordinate system of a unit is determined approximately by the position deduced by interpolation from a plurality of points, for example, three points on the wafer (cf S3). Thus, if the total errors $e$ obtained are organized according to the order of positions $P_{in}$ of individual dots on each unit coordinate system, a variation in total error $e$ over the whole stage can be grasped. FIG. 3 shows an example of the stage error in a unit, in which (a) exemplifies errors of the x- and y-axes and (b) exemplifies errors accumulated in the x- and y-axes.

(4) Then, correction of a coordinate was accomplished by mathematically subtracting the lately grasped total error $e$ composed of the stage error and the individual error from the unit coordinate of each unit (cf. S4), the coordinate linkage can be carried out with high accuracy even if the unit coordinate system employed in a particle test unit and that employed in a different analytical unit from the particle test unit differ from each other.

This series of computing means were performed with a computer.

Embodiment 2

Figure 4:
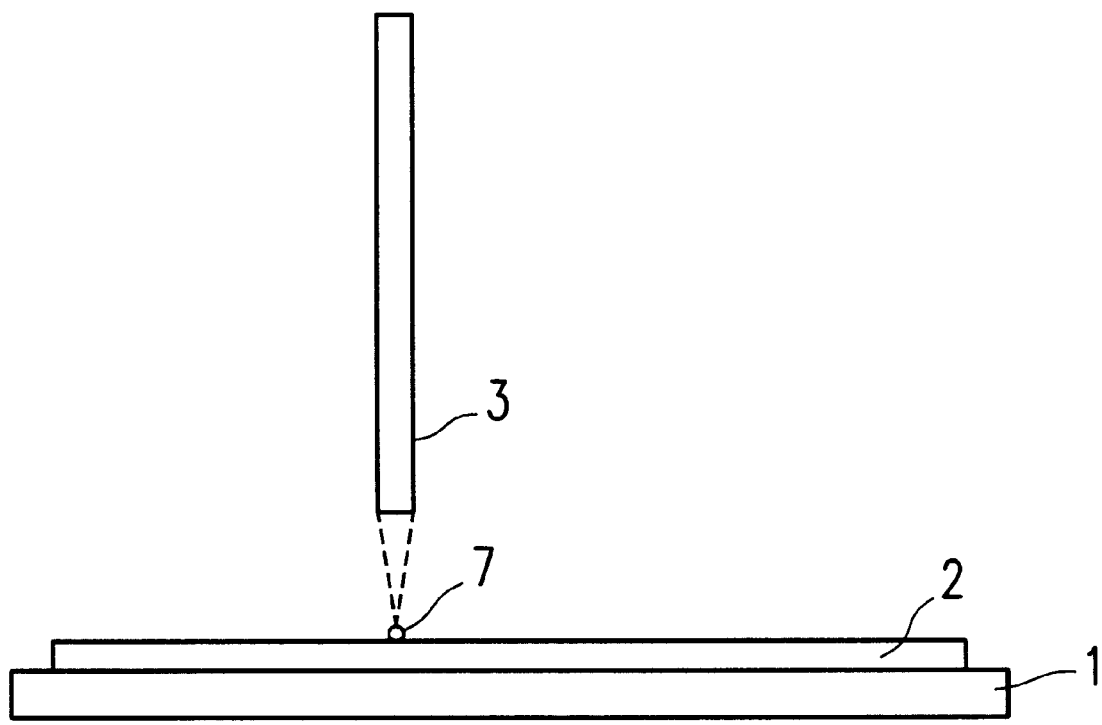
FIG. 4 shows an arrangement of using a metallographical microscope as an analytical unit in one embodiment of analytical method or analytical unit according to the present invention.

FIG. 4 is an explanatory drawing showing the fundamental arrangement of a metallographical microscope equipped with the actuator as an example of metallographical microscope provided with the function of coordinate linkage to be used in one embodiment of minute foreign substance observation method according to the present invention. The unit arrangement is the same as the fundamental arrangement of a conventional metallographical microscope equipped with the actuator, but the above-mentioned means for setting a common coordinate system is provided in a metallographical microscope according to the present invention.

First, for Surfscan 6200, a particle test unit available from Tencor Ltd., and a metallographical microscope equipped with the actuator, the total error $e$ on the unit coordinate of each unit were determined using one and the same standard wafer in accordance with the procedure shown in Embodiment 1. As a result, it was found that there was a deviation of about (±150 μm, ±150 μm) relative to any point on the x-y unit coordinate system for Surfscan 6200 and a deviation of about (±100 μm, ±100 μm) for a metallographical microscope equipped with the actuator.

Next, correction of the respective coordinates and linkage of the unit coordinate were accomplished by mathematically subtracting the lately determined total error $e$ for each point on the unit coordinates of individual units.

Then, using the same standard wafer, the degree of deviation in individual units was estimated again which revealed that it was improved to (±40 μm, ±40 μm) for the particle test unit and to (±15 μm, ±15 μm) for the metallographical microscope.

Next, the deviation was measured using a plurality of other standard wafers than the one employed above, which revealed that it can be confined within about (±80 μm, ±80 μm) and (±50 μm, ±50 μm), respectively, so that the effect of improvement was found to become somewhat worse.

Such being the case, an attempt was made to observe a minute foreign substance of 0.3 μm level present on a wafer used for production of a semiconductor element. As a result, the minute foreign substance can be confined within the extent of a visual field even at a 400 magnitude (the magnitude of an eyepiece and that of an objective are fixed to 20 and to 20, respectively) of the metallographical microscope and the microscopic observation of minute foreign substances of 0.3 μm level, though impossible formerly, became surely possible (they were observed as dark points).

Embodiment 3

With this embodiment, said means for correcting the unit coordinate provided at a conventional scanning laser microscope seen, for example, in RCM 8000 commercially available from Nicon K.K. is employed as an analytical unit in place of the metallographical microscope 3 of Embodiment 2. Accordingly, other constituents are quite the same as those shown in FIG. 4 and the coordinate linking method is also quite the same as with Embodiment 2.

Such being the case, an attempt was made to observe a minute foreign substance of 0.2 μm level present on a wafer used for production of a semiconductor element. As a result of observing each minute foreign substance by using UV rays for measurement, the surface observation of a foreign substance 7 could be fulfilled for minute foreign substances of 0.2 µm or larger diameter level and a dark point could be found for minute foreign substances 7 of less than 0.2 µm.

This embodiment, characterized in that the surface observation can be performed for a nondestructive test in the atmosphere, is effective especially for foreign substance analysis in the film forming step and the subsequent steps when applied to the production process of semiconductor elements or liquid crystal display elements.

Embodiment 4

With this embodiment, a conventional microscopic FTIR seen, for example, in microscopic IR unit IR-MAU 110 loaded JIR-5500 commercially available from Nippon Denshi K.K. is employed as an analytical unit in place of the metallographical microscope 3 of Embodiment 2 and aforesaid means for correcting a unit coordinate is provided similarly (a metallographical microscope is loaded on this unit). Accordingly, other constituents are quite the same as those shown in FIG. 4, the coordinate linking method is also quite the same as with Embodiment 2 and setting of minute foreign substances having a diameter down to 0.2 µm could be fulfilled.

Such being the case, an attempt was made to observe a minute foreign substance of 0.2 µm or higher levels present on a wafer used for production of a semiconductor element. As a result, since the wave length of infrared rays was long for a minute foreign substance on the order of 0.2 µm, no IR spectrum was obtained. However, when IR rays were applied to gradually larger size of foreign substances, the IR spectrum peculiar to organic substances was obtained for several foreign substances of 3 µm or larger levels and the generating cause of the foreign substances was found to depend on the failure of removal of a resist. In the production process of semiconductor elements or liquid crystal display elements, this analysis is effectively applied especially to the resist coating step or the subsequent steps.

Embodiment 5

With this embodiment, a conventional microscopic Raman seen, for example, in NR-1800 commercially available from Nippon Bunko K.K. is employed as an analytical unit in place of the metallographical microscope 3 of Embodiment 2 and aforesaid means for correcting a unit coordinate is provided similarly (a metallographical microscope is loaded on this unit). Accordingly, other constituents are quite the same as those shown in FIG. 4, the coordinate linking method is also quite the same as with Embodiment 2 and setting of minute foreign substances having a diameter down to 0.2 µm could be fulfilled.

Such being the case, an attempt was made to observe a minute foreign substance of 0.2 µm or higher levels present on a wafer used for production of a semiconductor element. As a result, no Raman spectrum was obtained from a minute foreign substance on the order of 0.2 µm, but the Raman spectrum peculiar to organic substances was obtained from several foreign substances of 1 µm or larger levels and the generating cause of the foreign substances was found to relate to film forming, etching and heat treatment. This analysis is effectively applied especially to the use in the steps related to film forming, etching and heat treatment among the production process of semiconductor elements or liquid crystal display elements.

Embodiment 6

With this embodiment, a conventional PL seen, for example, in 25C commercially available from Nippon Bunko K.K. is employed as an analytical unit in place of the metallographical microscope 3 of Embodiment 2 and aforesaid means for correcting a unit coordinate is provided similarly (a metallographical microscope is loaded on this unit). Accordingly, other constituents are quite the same as those shown in FIG. 4, the coordinate linking method is also quite the same as with Embodiment 2 and setting of minute foreign substances having a diameter down to 0.2 µm could be fulfilled.

Such being the case, an attempt was made to observe a minute foreign substance of 0.2 µm or higher levels present on a wafer used for production of a semiconductor element. As a result, no luminescence spectrum was obtained from a minute foreign substance on the order of 0.2 µm, but the fluorescence spectrum peculiar to organic substances was obtained from several foreign substances of 2 µm or larger levels and the generating cause of 2 µm or larger levels and the generating cause of the foreign substances was found to relate to film forming, etching and heat treatment. This analysis is effectively applied especially to the use in the steps related to film forming, etching and heat treatment among the production process of semiconductor elements or liquid crystal display elements.

Embodiment 7

With this embodiment, a conventional luminescence spectrometer seen, for example, in F-2000 commercially available from Hitachi Ltd. is employed as an analytical unit in place of the metallographical microscope 3 of Embodiment 2 and aforesaid means for correcting a unit coordinate is provided similarly (a metallographical microscope is loaded on this unit). Accordingly, other constituents are quite the same as those shown in FIG. 4, the coordinate linking method is also quite the same as with Embodiment 2 and setting of minute foreign substances having a diameter down to 0.2 µm could be fulfilled.

Such being the case, an attempt was made to observe a minute foreign substance of 0.2 µm or higher levels present on a wafer used for production of a semiconductor element. As a result, no luminescence spectrum was obtained from a minute foreign substance on the order of 0.2 µm, but the luminescence spectrum peculiar to organic substances was obtained from several foreign substances of 2 µm or larger levels and the generating cause of the foreign substances was found to relate to film forming, etching and heat treatment. This analysis is effectively applied especially to the use in the steps related to film forming, etching and heat treatment among the production process of semiconductor elements or liquid crystal display elements.

Embodiment 8

Figure 5:
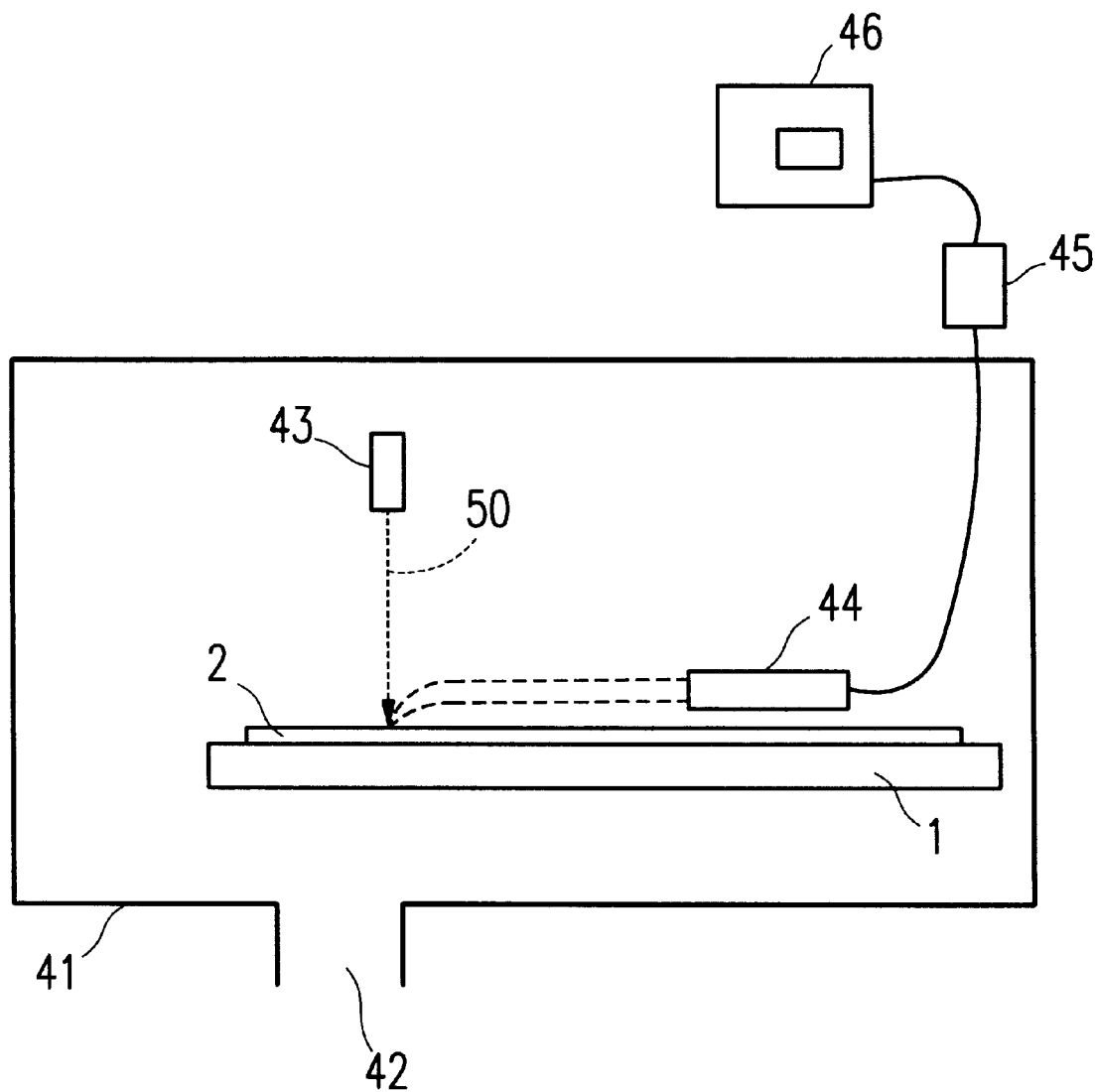
FIG. 5 shows an arrangement of using a length measuring SEM as an analytical unit in one embodiment of analytical method or analytical unit according to the present invention.

FIG. 5 is an explanatory drawing of the fundamental arrangement of another embodiment of minute foreign substance analytical method according to the present invention. The difference of this embodiment from Embodiment 2 lies in that a conventional length measuring SEM seen, for example, in S-7000 commercially available from Hitachi Ltd. is employed as an analytical unit in place of the metallographical microscope 3 of Embodiment 2 employed in FIG. 4 and aforesaid means for correcting a unit coordinate is provided similarly (the x-y stage to be employed differs from that of Embodiment 2).

With this embodiment, as shown in FIG. 5, the analytical unit comprises an electron gun unit 43 provided with an electron gun for applying scanning electron beam 50 to a silicon wafer 2 and with an electron lens, and a secondary electron detector 44 for converting secondary electrons generated from a silicon wafer 2 into an electric signal. A signal obtained from the secondary electron detector 44 is sent to an amplifier/control unit 45 for the amplification of electric signals and the control and displayed by a CRT 46 for outputting a secondary electron image. A chamber 41 is provided for keeping these constituents in vacuum, is evacuated through an exhaust hole 42 into vacuum and kept at vacuum. Using this length measuring SEM in accordance with quite the same procedure, the test of a minute foreign substance 7 present on a silicon wafer 2 can be performed. That is, in accordance with the procedure described in Embodiment 1, the total error $\underline{e}$ on the unit coordinate system of a length measuring SEM was determined using one and the same standard wafer and subtracted mathematically from the unit coordinate, and the coordinate correction was performed for the result.

Next, as with Embodiment 2, a deviation generated by the coordinate linkage was examined by using a plurality of standard wafers, which revealed that it can be confined within about ($\pm 50\,\mu m$, $\pm 50\,\mu m$) for the origin position or the center position and for any point definable in the wafer in the representation of x-y coordinate. A considerable effect of improvement was found to be obtained.

Such being the case, an attempt was made to observe a minute foreign substance of 0.1 $\mu m$ level present on a wafer used for production of a semiconductor element. According to this embodiment, a minute foreign substance 7 could be found within the visual field (2000 magnitude) of the SEM and a distinct SEM image could be obtained. There were minute foreign substances of various shapes, such as a concave shape and convex shape, and their shapes could be grasped. In the production process of semiconductor elements or liquid crystal display elements, analysis in this embodiment is effectively applied effectively to all steps of film forming, etching, cleansing, exposure, ion injection, diffusion and heat treatment.

Embodiment 9

Figure 6:
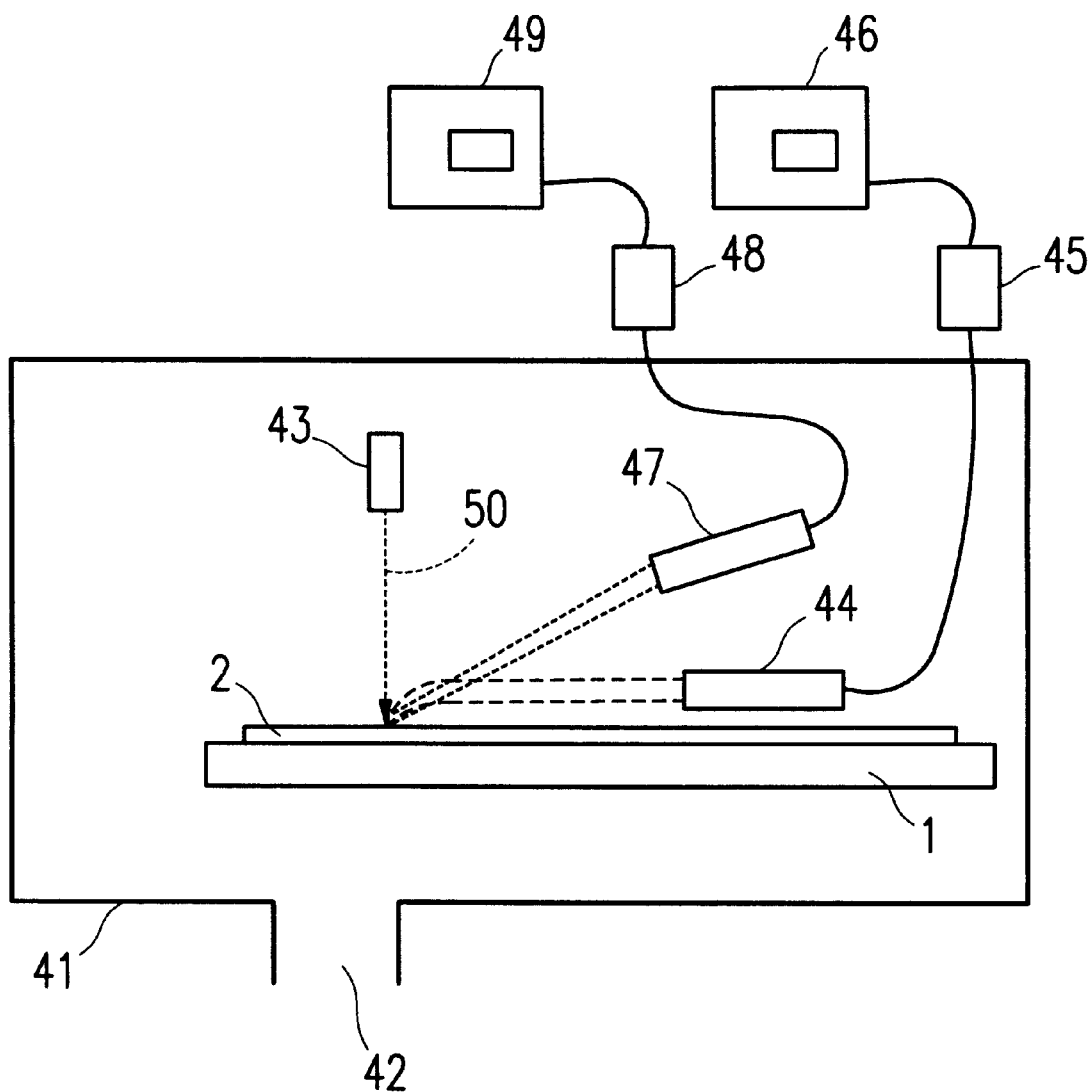
FIG. 6 shows an arrangement of using an EPMA provided with the positioning function as an analytical unit in one embodiment of analytical method or analytical unit according to the present invention.

FIG. 6 is an explanatory drawing of the fundamental arrangement of yet another embodiment of minute foreign substance analytical method according to the present invention. This embodiment is formed by further adding an X-ray detector 47, an amplifier/control unit 48 for the amplification/control of electric signals brought about from the X-ray detector 47, and a CRT 49 for displaying an X-ray output to the SEM-used analytical unit according to Embodiment 8. An EPMA is formed in this way but the arrangement of other components is the same as that of Embodiment 8. The coordinate linkage method including the provision of means for correcting a unit coordinate is also quite the same as with Embodiment 8. In according with quite the same procedure as with Embodiment 8, the test of a minute foreign substance 7 present on the surface of the same silicon wafer 2 was performed. As a result, the element analysis could be accomplished for convex minute foreign substances 7 and the minute foreign substances were found to be compounds of W, Cu, Fe, C, S, O, Cl and the like. However, for a minute foreign substance 7 of 0.3 $\mu m$ or smaller, a considerable length of detection time was necessary to execute a detailed element analysis.

In the production process of semiconductor elements or liquid crystal display elements, analysis in this embodiment is effectively applied especially to all steps of film forming, etching, cleansing, exposure, ion injection, diffusion and heat treatment.

Embodiment 10

With this embodiment, an AES is employed as an analytical unit in place of the EPMA of Embodiment 9, the arrangement of other components is quite the same as that shown in FIG. 6, and means for correcting a unit coordinate and the operation method thereof are the same as with Embodiment 8. As the AES, for example, PHI-670 available from Barkin Elmer Ltd. can be employed. As with the all above embodiments, minute foreign substances 7 present on the surface of a silicon wafer 2 were analyzed using this unit. As a result, the element analysis could be accomplished for convex minute foreign substances 7. From the composition analysis of minute foreign substances, compounds of W, Cu, Fe, C, S, O and Cl could be distinguished and the generating source of dust could be identified to take measures against the generation of dust. In the production process of semiconductor elements or liquid crystal display elements, analysis by this embodiment is effectively applied especially to all steps of film forming, etching, cleansing, exposure, ion injection, diffusion and heat treatment.

Embodiment 11

With this embodiment, an EELS is employed as an analytical unit in place of the EPMA of Embodiment 9, the arrangement of other components is quite the same as that shown in FIG. 6, and means for correcting a unit coordinate and the operation method thereof are the same as with Embodiment 8. As the EELS, for example, PHI-660 available from Barkin Elmer Ltd. can be employed. As with the all above embodiments, minute foreign substances 7 present on the surface of a silicon wafer 2 were analyzed using this unit. As a result, the element analysis could be accomplished for convex minute foreign substances 7, chemical bonding states of minute foreign substances 7 were elucidated and the generating source of dust could be identified to take measures against the generation of dust. In the production process of semiconductor elements or liquid crystal display elements, analysis by this embodiment is effectively applied especially to the steps of film forming, etching and exposure.

Embodiment 12

Figure 7:
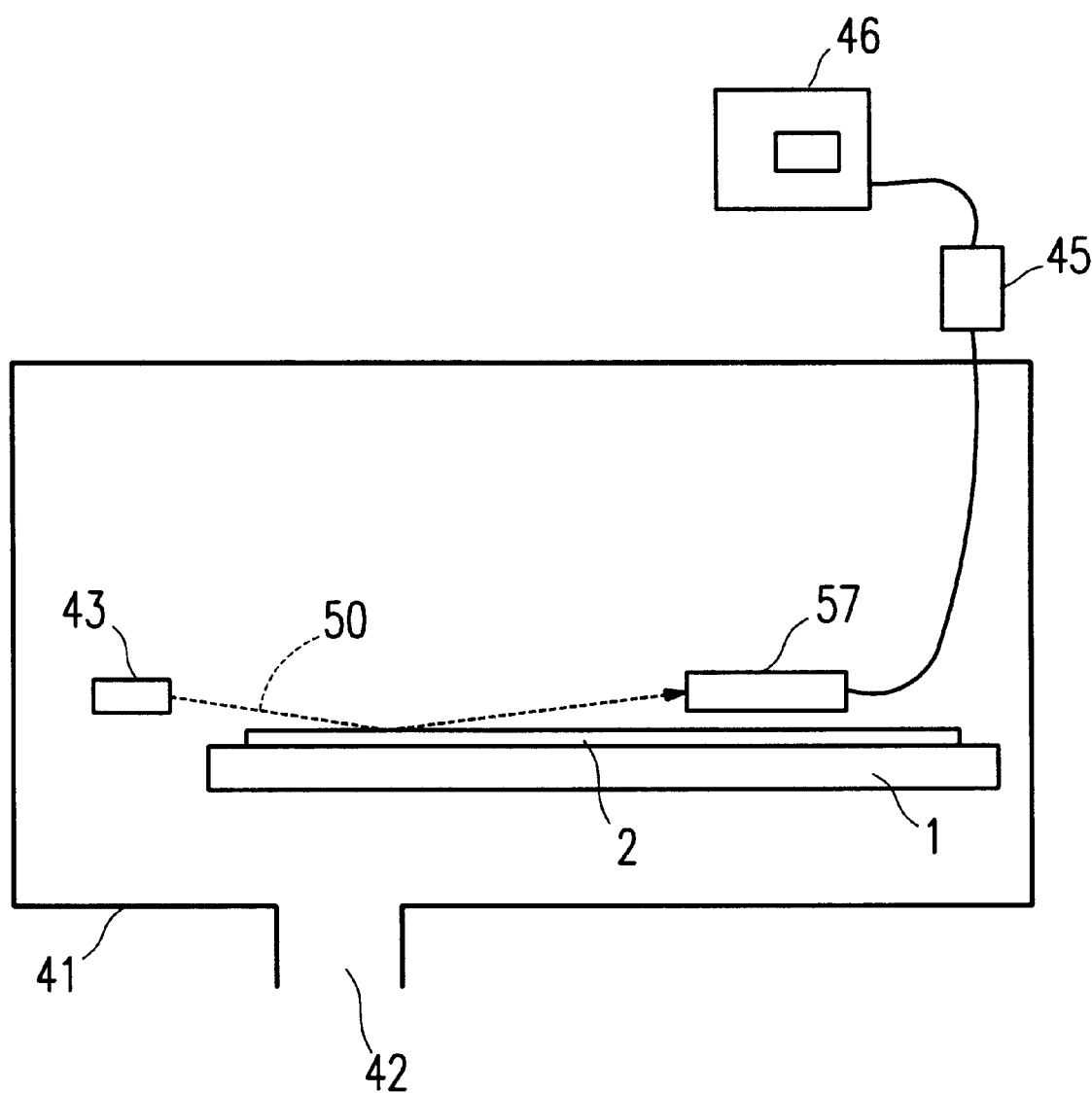
FIG. 7 shows an arrangement of using a RHEED as an analytical unit in one embodiment of analytical method or analytical unit according to the present invention.
Figure 8:
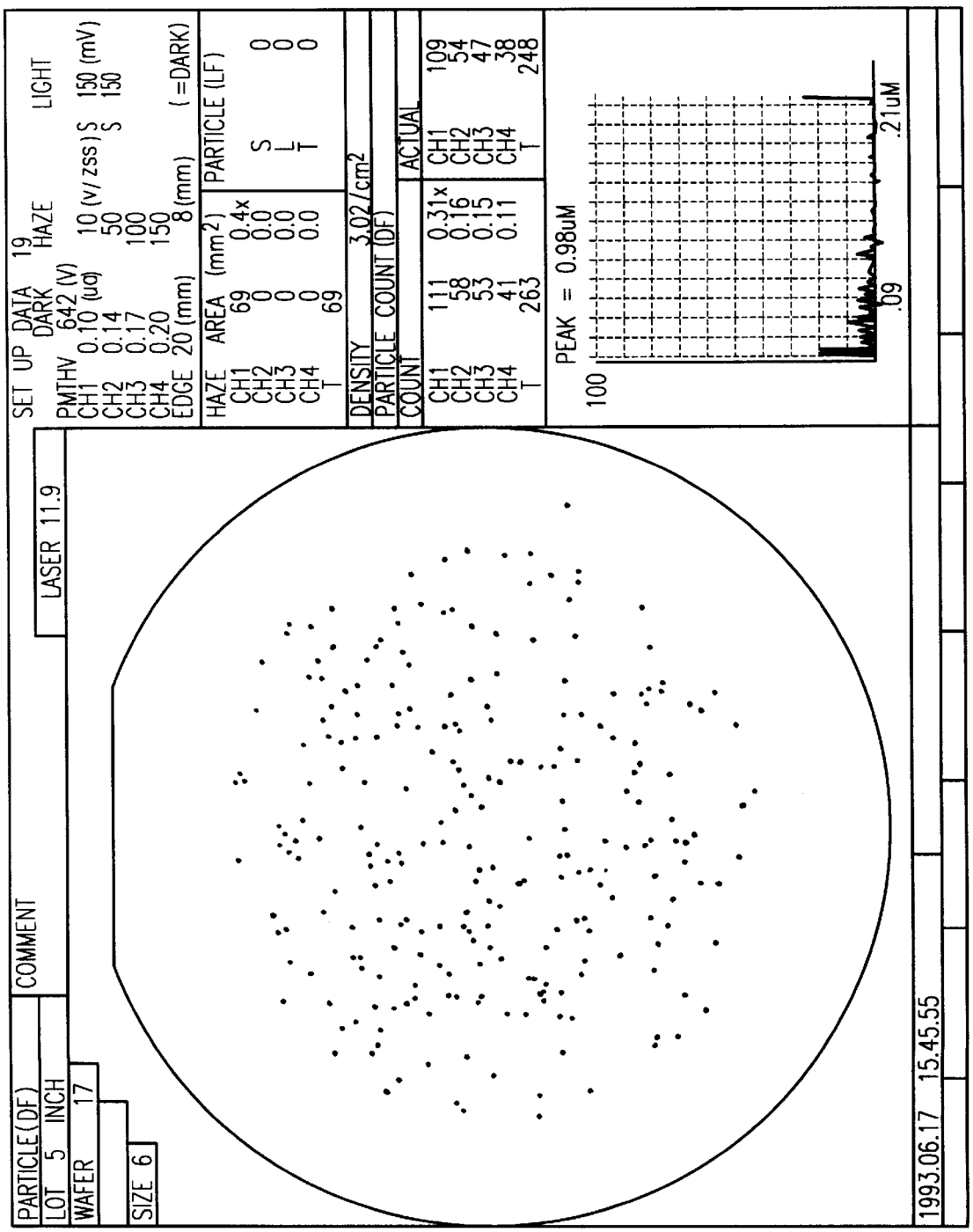
FIG. 8 shows one example of measured results of foreign substances on a silicon wafer in a particle test unit.
Figure 9A:
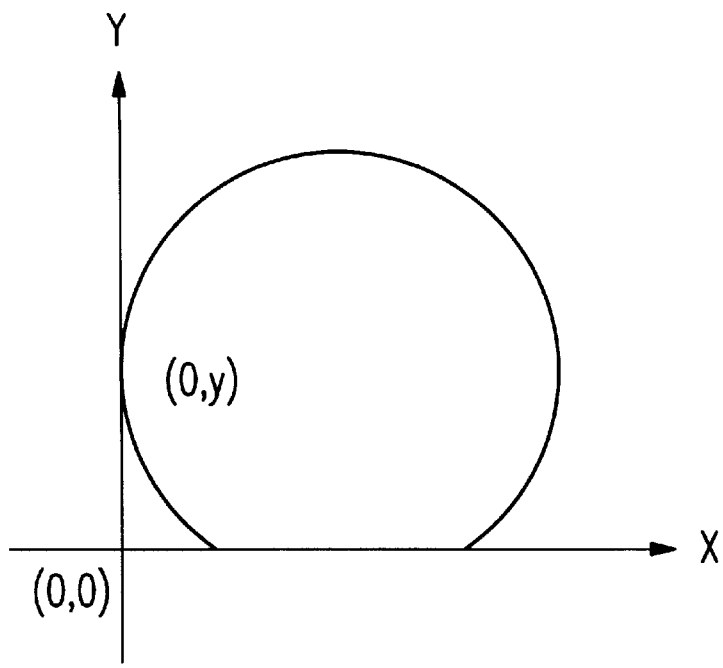
FIG. 9 shows one definition example of unit coordinate employed for a conventional test unit and analytical unit.
Figure 9B:
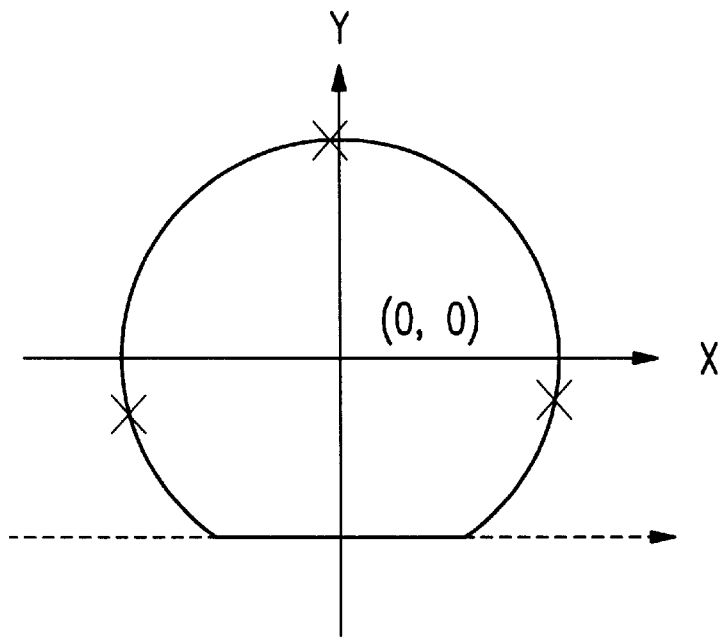

FIG. 7 is an explanatory drawing of the fundamental arrangement of RHEED in still another embodiment of minute foreign substance analytical method according to the present invention. This embodiment differs from Embodiment 8 in that the electron gun unit 43 is provided in the same angle as the slant angle of a secondary electron detector 44 to the surface of a silicon wafer 2 at such a position that electron beams 50 fall close to the surface of a silicon wafer 2 and a CCD camera 57 is attached for obtaining a diffraction spot generated by electron beam 50 diffracted on the surface of the silicon wafer 2, and is common otherwise.

As a result of testing a minute foreign substance 7 present on the surface of the silicon wafer 2 by using this embodiment as with the all above embodiments, diffraction spots could be obtained for several minute foreign substances 7, they were found to be crystalline materials and such crystalline materials as, e.g., whisker could be prevented. If used especially after the film forming and heat treatment in the production process of semiconductor elements or liquid crystal display elements, analysis by this embodiment is effective for preventing the anomalous growth of crystals and for selecting the preventing conditions.

Embodiment 13

With this embodiment, an SIMS is employed as an analytical unit in place of the EPMA of Embodiment 9, that is, an ion gun unit comprising an ion gun and a condenser lens is employed in place of the electron gun unit 43 of Embodiment 8, scanning ion beams are irradiated onto the surface of a silicon wafer 2 in place of electron beams emitted from the electron gun 50, and a mass spectrometer unit comprising a double focus mass spectrometer, a quadruple mass spectrometer or the like is employed to separate and detect a secondary ion generated on the surface of the silicon wafer 2. The arrangement of other components is quite the same as that shown in FIG. 6, and means for correcting a unit coordinate and the coordinate linking method is quite the same as with Embodiment 9.

As SIMS, for example, IMS-5F available from CAMECA may be employed.

As a result of testing a minute foreign substance 7 present on the surface of the silicon wafer 2 by using this embodiment as with the all above embodiments, the composition analysis could be accomplished for convex minute foreign substances 7, the generating cause of minute foreign substances was disclosed and the deterioration of electric characteristics due to the diffusion of metals from foreign substances was found to affect a decrease in yield. In the production process of semiconductor elements or liquid crystal display elements, this analysis is effectively applied especially to steps of film forming, etching, cleansing and heat treatment.

Embodiment 14

With this embodiment, a TOF-SIMS is employed in place of the SIMS of Embodiment 13, a mass spectrometer unit comprising a time of flight-SIMS is employed in place of a mass spectrometer unit comprising a double focus mass spectrometer, a quadruple mass spectrometer or the like, the arrangement of other components is quite the same as that shown in FIG. 4, and means for correcting a unit coordinate and the coordinate linking method is quite the same as with Embodiment 9.

According to this embodiment, the chemical structure of foreign substances can be analyzed by analyzing fragments of individual foreign substances. Unlike Embodiment 13, this embodiment has an effect on analyzing materials of high molecular weight present on the utmost surface of a foreign substance. Thus, this embodiment is effective especially for the analysis of foreign substances containing organic matter and the like.

Embodiment 15

With this embodiment, a PIXE is employed in place of the SIMS of Embodiment 13, and further an X-ray detector, an amplifier/control unit for amplifying/controlling an electric signal produced from the X-ray detector and a CRT for outputting an X-ray image are added to the arrangement of Embodiment 13 to constitute a PIXE apparatus.

According to this embodiment, the composition analysis of individual foreign substances can be carried out, this embodiment is suitable especially for highly sensitive and highly accurate element analysis and therefore effective especially for analyzing a foreign substance of 0.1 µm or smaller sizes.

Embodiment 16

With this embodiment, a FIB is employed as an analytical unit in place of the X-ray detector of Embodiment 8, that is, an ion gun unit comprising an ion gun and a condenser lens is employed in place of the electron gun unit 43 of Embodiment 8, and the FIB capable of treatment for removing impurities is made up by irradiating scanning ion beam to the surface of a wafer 2 in place of electron beams emitted from the electron gun 50. The arrangement of other components is quite the same as that shown in FIG. 5, and the coordinate linking means and method are quite the same as with Embodiment 8.

According to this embodiment, it is possible not only to observe a minute foreign substance but also to remove an unnecessary foreign substance and there is the effect of immediate repair. Thus, this embodiment is effective especially for a yield promotion by a repair of failure originating in foreign substances.

Embodiment 17

With this embodiment, an XPS using soft X-ray such as AlKα or MgKα is employed in place of the electron gun unit 43 of Embodiment 9, the arrangement of other components is quite the same as that shown in FIG. 6, and a coordinate linking method and the like are the same as with Embodiment 9.

According to this embodiment, the chemical bonding could be analyzed for convex minute foreign substances 7. Especially because of using soft x-ray beams, this embodiment has an effect of a slight damage on samples and therefore is effective especially for the nondestructive analysis in the tens of angstroms depth from the utmost surface of a foreign substance.

Embodiment 18

With this embodiment, an UPS using UV beams obtained by making UV rays generated from a high-tension mercury lamp into the shape of beam is employed in place of the electron gun unit 43 of Embodiment 9, the arrangement of other components is quite the same as that shown in FIG. 6, and coordinate linking means and method and the like are the same as with Embodiment 9.

According to this embodiment, the chemical bonding could be analyzed for convex minute foreign substances 7. Especially because of using UV beams, this embodiment has an effect of a slight damage on samples and therefore is effective especially for the nondestructive composition analysis in the tens of angstroms depth from the utmost surface of a foreign substance.

Embodiment 19

With this embodiment, for example, a probe microscope SPA 350 (the AFM probe is used as a probe) available from Seiko Denshi Kogyo K.K. is employed as an analytical unit in place of the metallographical microscope 3 of Embodiment 2, so that the arrangement of other components is quite the same as that shown in FIG. 4, and coordinate linking means and method are the same as with Embodiment 2. This embodiment is featured by enabling the surface observation in the atmosphere.

Such being the case, an attempt was made to observe a minute foreign substance of 0.1 µm level present on a wafer used for production of a semiconductor element. According to this embodiment, a minute foreign substance 7 could be easily found within the scan range (80 µm) of the AFM and a distinct AFM image could be obtained. There were minute foreign substances of various shapes, such as a concave shape and convex shape, and their shapes could be grasped. In the production process of semiconductor elements or liquid crystal display elements, analysis in this embodiment is effectively applied especially to all steps of film forming, etching, cleansing, exposure, ion injection, diffusion and heat treatment.

Embodiment 20

With this embodiment, for example, a probe microscope SPA 350 (the STM probe is used as a probe) available from Seiko Denshi Kogyo K.K. is employed as an analytical unit in place of the metallographical microscope 3 of Embodiment 2, so that the arrangement of other components is quite the same as that shown in FIG. 4, and coordinate linking means and method are the same as with Embodiment 2. This embodiment is featured by enabling the surface observation in the atmosphere.

Such being the case, an attempt was made to observe a minute foreign substance of 0.1 $\mu$m level present on a wafer used for production of a semiconductor element. According to this embodiment, a minute foreign substance 7 could be easily found within the scan range (80 $\mu$m) of the STM and a distinct STM image could be obtained. There were minute foreign substances of various shapes, such as a concave shape and convex shape, and their shapes could be grasped. In the production process of semiconductor elements or liquid crystal display elements, analysis in this embodiment is effectively applied especially to all steps of film forming, etching, cleansing, exposure, ion injection, diffusion and heat treatment.

Embodiment 21

With this embodiment, for example, a probe microscope SPA 350 (the MFM probe is used as a probe) available from Seiko Denshi Kogyo K.K. is employed as an analytical unit in place of the metallographical microscope 3 of Embodiment 2, so that the arrangement of other components is quite the same as that shown in FIG. 4, and coordinate linking means and method are the same as with Embodiment 2. This embodiment is featured by enabling the surface observation in the atmosphere.

Such being the case, an attempt was made to observe a minute foreign substance of 0.1 $\mu$m level present on a wafer used for production of a semiconductor element. According to this embodiment, a minute foreign substance 7 could be easily found within the scan range (80 $\mu$m) of the MFM, a distinct MFM image could be obtained and the generating cause of foreign substances was disclosed. In the production process of semiconductor elements or liquid crystal display elements, this analysis is effectively applied especially to steps of film forming, etching, cleansing and heat treatment.

Control 1

Using a particle test unit, Surfscan 6200 available from Tencor Ltd. and a length measuring SEM, S-7000 available from Hitachi Ltd., deviations generated were examined with a plurality of standard wafers after the linkage of unit coordinate systems made between the units, which revealed that they can be confined within about ($\pm 150$ $\mu$m $\pm 150$ $\mu$m) for the origin position or the center position and for any point definable in the wafer in the representation of x-y coordinate.

According to the minute foreign substance analytical method of the present invention, since the unit coordinate in at least either one of a particle test unit and an analytical unit is corrected by using a standard wafer or the unit coordinates between both units are linked via a standard wafer, the total error equal to the sum of the stage error potentially present in a unit coordinate and indefinite individual errors originating in peculiarities of the respective units can be eliminated and a deviation generated when linking the unit coordinate of a conventional particle unit and that of an analytical unit can be radically reduced. Consequently, the position detected by the particle test unit for a minute foreign substance can be readily and surely set within the visual field of the analytical unit by individually operating the unit coordinates of both units.

Thus, even a minute foreign substance that has so far been difficult to detect in a sample of wide area, can be detected at a high magnification and a minute foreign substance can be set in the visual field of the analytical unit. Furthermore, since the surface observation, composition observation and the like can be selectively carried out only for the range within which the minute foreign substance is present, the measuring time can be greatly shortened and the quality estimation of a sample can be accomplished.

In addition, according to the analytical unit of the present invention, since means for correcting the total error potentially present in a unit coordinate is provided on the basis of the scale of a standard wafer, the influence of the total error(s) of the particle test unit and/or the analytical unit can be reduced and the minute foreign substance detected by the particle test unit with its unit coordinate can be in a short time and surely set within the visual field of the analytical unit by using the unit coordinate of the analytical unit.

Furthermore, since the aforesaid means for correcting the coordinate of a sample on the basis of a standard wafer is provided in each of various analytical units mentioned above, the minute foreign substance detected by the particle test unit can be easily set within the visual field of each analytical unit and the analytical unit corresponding to the object can be utilized as an analytical unit, so that the surface shape, element analysis, chemical structure, crystalline structure and like of the minute foreign substance can be analyzed and moreover the surface treatment can be also performed.

Furthermore, by applying the analytical method and analytical unit of the present invention to the production process of semiconductor elements or the production process of liquid crystal display elements, the presence of foreign substances can be prevented from affecting a fine pattern, so that a semiconductor element or a liquid crystal display element improved in yield and reliability can be obtained.

What is claimed is:

1. A standard wafer to be used for linking coordinate systems between different units in a minute foreign substance analysis method, the standard wafer comprising:

a substrate defining a surface; and an array of relatively positioned dots drawn on a surface of the substrate.

2. A standard wafer according to claim 1, wherein the array of relatively positioned dots is formed from a plurality of array segments of relatively positioned dots.

3. A standard wafer according to claim 1, wherein the dots include at least a first group of dots having a first predetermined diameter and a second group of dots having a second predetermined diameter greater than the first predetermined diameter.

4. A standard wafer according to claim 1, wherein the dots are relatively positioned in an array having a plurality of array segments.

5. A standard wafer according to claim 4, wherein the dots include at least a first group of dots having a first predetermined diameter and a second group of dots having a second predetermined diameter greater than the first predetermined diameter.

6. A standard wafer according to claim 1, wherein the dots in the array are provided randomly, and a relative positional relation between the respective dots is known.

7. A standard wafer according to claim 1, wherein the dots in the array have a relative positional relation determined by a function defined digitally.

8. A standard wafer according to claim 1, wherein the array includes at least one circle and the dots are provided along the circle for every predetermined angle.

9. A standard wafer according to claim 1, wherein the array includes at least one rectangular-coordinated axis and the dots are provided along the rectangular-coordinate axis for every predetermined angle.

10. A standard wafer according to claim 1, wherein the array includes at least on circle and at least one rectangular-coordinate axis, the dots being provided along the circle for every predetermined angle and along the rectangular-coordinate axis for every predetermined angle.

* * * * *